United States Patent [19]

Szántay et al.

[11] 4,285,865
[45] Aug. 25, 1981

[54] PROCESS FOR THE PREPARATION OF HALOGENATED 15-HYDROXY-E-HOMOEBURNANE COMPOUNDS

[75] Inventors: Csaba Szántay; Lajos Szabó; György Kalaus; Lajos Dancsi; Tibor Keve; Ferenc Drexler, all of Budapest, Hungary

[73] Assignee: Richter Gedeon Vegyeszeti Gyar Rt, Budapest, Hungary

[21] Appl. No.: 175,385

[22] Filed: Aug. 5, 1980

[30] Foreign Application Priority Data

Aug. 6, 1979 [HU] Hungary .................. RI 721

[51] Int. Cl.$^3$ .................. C07D 487/14; C07D 487/16
[52] U.S. Cl. .................. 260/239.3 P; 424/256; 260/245.7
[58] Field of Search .................. 260/239.3 P, 245.7; 424/256

[56] References Cited
FOREIGN PATENT DOCUMENTS
2010833 7/1979 United Kingdom .............. 260/239.3 P

*Primary Examiner*—Robert T. Bond
*Attorney, Agent, or Firm*—Karl F. Ross

[57] ABSTRACT

The invention relates to new, racemic or optically active, halogenated 15-hydroxy-E-homoeburnane derivatives of the general formula (Ia) and/or (Ib),

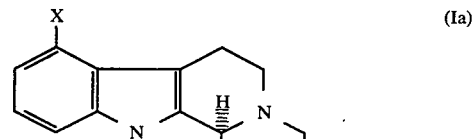

(Ia)

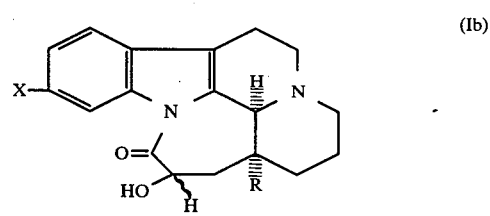

(Ib)

wherin R is a $C_{1-6}$ alkyl group and X is halogen, and acid addition salts thereof. These compounds are biologically active, furthermore they can be applied as intermediates in the synthesis of other pharmaceutically active substances.

The compounds of the general formulae (Ia) and (Ib) are prepared by halogenating the respective racemic or optically active 15-hydroxy-E-homoeburnane derivative of the general formula (II), wherein R is as defined above.

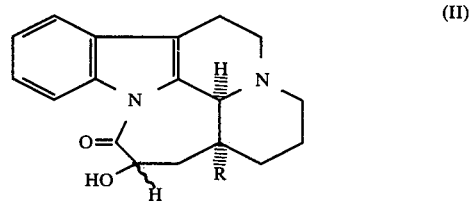

(II)

4 Claims, No Drawings

PROCESS FOR THE PREPARATION OF HALOGENATED 15-HYDROXY-E-HOMOEBURNANE COMPOUNDS

The invention relates to a process for preparing new, racemic or optically active, halogenated 15-hydroxy-E-homoeburnane derivatives of the formulae (Ia) and/or (Ib),

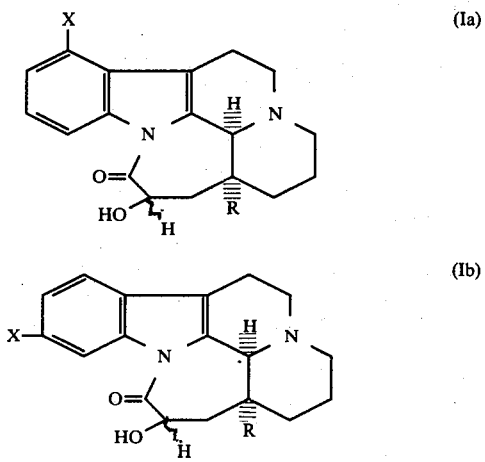

wherein R is a $C_{1-6}$ alkyl group and X is halogen, and acid addition salts thereof.

The new compounds defined above are prepared according to the invention so that a racemic or optically active 15-hydroxy-E-homoeburnane derivative of the formula (II),

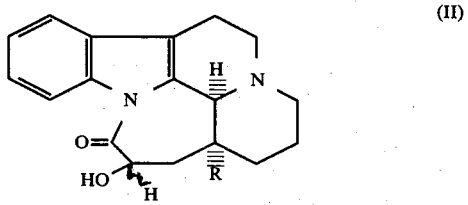

wherein R is as defined above, or an acid addition salt thereof is treated with a halogenating agent. If desired, the compounds of the formulae (Ia) and (Ib) formed in the reaction are separated from one another, and then any of the compounds is converted into its acid addition salt and/or resolved, if desired.

The new compounds according to the invention can be utilized as intermediates in the preparation of pharmaceutically active compounds, such as halovincaminic acid esters. The new compounds according to the invention also possess valuable biological effects.

In the compounds of the formulae (Ia) and (Ib) R may represent a straight-chain or branched $C_{1-6}$ alkyl group, such as methyl, ethyl, n-propyl, isopropyl, n-butyl, sec.-butyl, tert.-butyl, n-pentyl, isopentyl, n-hexyl or isohexyl group. R is preferably an ethyl or n-butyl group.

X may represent all the four halogens, i.e. fluorine, chlorine, bromine and iodine, preferably bromine.

The starting substances of the formula (II) can be prepared by the method described in Tetrahedron 33, 1803 (1977).

The starting substances of the formula (II) are halogenated with reactants capable of introducing a halogen atom into the unsaturated ring without simultaneously replacing the 15-hydroxy group by a halogen. It is preferred to use elemental halogens as halogenating agents.

According to a preferred method of the invention compounds of the formulae (Ia) and (Ib) in which X stands for bromine are prepared. The corresponding starting substances of the formula (II) are brominated preferably with elemental bromine, but other brominating agents leading to the formation of the required bromo compound can also be used.

Bromination is performed in an inert organic solvent or solvent mixture. Of the solvents usable in this step, e.g. the following are to be mentioned: non-polar organic solvents, such as halogenated aliphatic hydrocarbons (e.g. chloroform, dichloromethane, dichloroethane, etc.), furthermore polar organic solvents, such as organic acids (e.g. glacial acetic acid, propionic acid, etc.).

In some instances it is preferred to perform bromination in the presence of a Lewis acid. As the Lewis acid e.g. ferric chloride, zinc chloride, aluminum chloride, stannic chloride, antimony tetrachloride, or boron trifluoride can be used.

Bromination can be performed at temperatures of 20° to 40° C., preferably at room temperature.

The ratio of the stereoisomers formed in the reaction depends on the rate of bromine administration.

When brominating a compound of the formula (II), a mixture of the compounds of the formulae (Ia) and (Ib) is obtained. The two stereoisomer bromine derivatives can be separated from one another by methods known per se, such as crystallization, salt formation and separation, or preparative layer chromatography. It is preferred to use Merck PF 254+366 grade silica gel as adsorbent in the preparative layer chromatography. Various solvent combinations can be utilized as running and eluting agents.

The compounds of the formulae (Ia) and/or (Ib) can be reacted with various acids to form the respective acid addition salts. Of the acids applicable in this reaction, e.g. the following are to be mentioned: mineral acids, such as hydrogen halides (e.g. hydrochloric acid or hydrogen bromide), sulfuric acid, phosphoric acid, nitric acid, perhaloic acids (e.g. perchloric acid), etc., organic carboxylic acids, such as formic acid, acetic acid, propionic acid, glycolic acid, maleic acid, hydroxymaleic acid, fumeric acid, salicylic acid, lactic acid, cinnamic acid, benzoic acid, phenylacetic acid, p-aminobenzoic acid, p-hydroxybenzoic acid, p-aminosalicylic acid, etc., alkylsulfonic acids, such as methanesulfonic acid, ethanesulfonic acid, etc., cycloaliphatic sulfonic acids, such as cyclohexylsulfonic acid, arylsulfonic acids, such as p-toluenesulfonic acid, naphthylsulonic acid, sulfanylic acid, etc., amino acids, such as aspartic acid, glutamic acid, etc.

If desired, the racemic compounds of the formulae (Ia) and/or (Ib) can be resolved in a manner known per se to obtain the respective optically active derivatives. Optically active end-products can also be obtained, however, when an optically active compound of the formula (II) is used as the starting substance.

If desired, the racemic or optically active compounds of the formulae (Ia) and/or (Ib), as well as the acid addition salts thereof can be subjected to further purification steps, such as recrystallization from an appropriately selected solvent or solvent mixture. The solvents or solvent mixtures utilized in this step are chosen in accordance with the solubility and crystallization characteristics of the substance to be purified.

The process of the invention yields the end-products in forms easy to identify. The IR spectra, NMR spectra and mass spectra of the compounds prepared are in harmony with the assigned structures.

The invention is elucidated in detail by the aid of the following non-limiting Examples.

EXAMPLE 1

($\pm$)-9-Bromo-14-oxo-15-hydroxy-E-homoeburnane-(3α,17α) and ($\pm$)-11-bromo-14-oxo-15-hydroxy-E-homoeburnane-(3α,17α)

(a) 1.1 g of ferric chloride hexahydrate are added to a solution of 1.30 g (4.01 mmoles) of ($\pm$)-14-oxo-15-hydroxy-E-homoeburnane-(3α,17α), melting at 193°-195° C., in 15 ml of glacial acetic acid, and 5 ml of a 1 molar bromine solution in glacial acetic acid are added dropwise to the mixture at room temperature under constant stirring. The bromine solution is introduced slowly, at a rate of 0.5 ml/min. When the addition is complete the mixture is stirred for additional 9 hours at room temperature. When the reaction terminates 200 ml of water are added to the suspension, and the pH of the resulting mixture is adjusted to 5 with 25% aqueous ammonia. The mixture is extracted with 100, 80 and 60 ml of dichloromethane. The organic solutions are combined, admixed with 100 ml of water, and the pH of the mixture is adjusted to 10 with 25% aqueous ammonia. The two-phase mixture is shaken, thereafter the dichloromethane phase is separated, washed thrice with 100 ml of water, each, dried over anhydrous solid magnesium sulfate, filtered, and the filtrate is evaporated to dryness in vacuo.

The 1.4 g of dry residue obtained are subjected to preparative thin layer chromatography. Kieselgel PF$_{254+366}$ grade silica gel plates, 20×20 cm in area and 1.5 mm in thickness, are applied as adsorbent, and a 10:3 mixture of benzene and acetonitrile is applied as solvent. The eluted substances are crystallized from methanol.

0.15 g (11%) of ($\pm$)-9-bromo-14-oxo-15-hydroxy-E-homoeburnane-(3α,17α) are isolated from the upper spot. The substance melts at 202°-203° C. The empirical formula of the product is $C_{20}H_{23}BrN_2O_2$(mol.wt.: 403.33).

IR spectrum (KBr): $\nu_{max}$. 3410 cm$^{-1}$ (—OH), 1685 cm$^{-1}$ (amide —CO).

NMR spectrum (deuterochloroform): δ=0.97 (t, 3H, CH$_3$), 7.21-8.64 (m, 3H, aromatic protons).

$C_{10}$-H=7.51 ppm, $J_{11,12}$=7.8 Hz (ortho)
$C_{11}$-H=7.21 ppm, $J_{11,10}$=7.6 Hz (ortho)
$C_{12}$-H=8.64 ppm, $J_{10,12}$=1.9 Hz (meta).

Mass spectrum (m/e): 404, 403, 402, 401, 376, 374, 360, 358, 347, 345, 332, 330, 317, 315, 303, 301, 277, 275, 180, 167, 153, 140.

0.63 1 g (46.1%) of ($\pm$)-11-bromo-14-oxo-15-hydroxy-E-homoeburnane-(3α,17α) are isolated from the middle spot. The substance melts at 195°-197° C. The empirical formula of the product is $C_{20}H_{23}BrN_2O_2$ (mol.wt.: 403.33).

IR spectrum (KBr): $\nu_{max}$. 3350 cm$^{-1}$ (—OH), 1680 1 cm$^{-1}$ (amide —CO).

NMR spectrum (deuterochloroform): δ=0.95 1 (t, 3H, CH$_3$), 7.25-8.69 (m, 3H, aromatic protons) ppm.
$C_9$-H=7.25 ppm, $J_{10,12}$=1.9 Hz (meta)
$C_{10}$-H=7.39 ppm, $J_{10,9}$=7.7 Hz (ortho)
$C_{12}$-H=8.69 ppm, $J_{9,12}$=0.3 Hz (para)

Mass spectrum (m/e): 404, 403, 402, 401, 376, 374, 360, 358, 347, 345, 332, 330, 317, 315, 303, 301, 277, 275, 180, 167, 153, 140.

0.2 g of the starting substance, ($\pm$)-14-oxo-15-hydroxy-E-homoeburnane-(3α,17α) are recovered from the lower spot.

(b) 1.1 g of ferric chloride hexahydrate are added to a solution of 1.3 1 g (4.01 mmoles) of ($\pm$)-14-oxo-15-hydroxy-E-homoeburnane-(3α, 17α), melting at 193°-195° C., in 15 ml of glacial acetic acid, and 5 ml of a 1 molar bromine solution in glacial acetic acid are added to the mixture in a single portion at room temperature under constant stirring. The reaction mixture is stirred at room temperature for additional 9 hours, thereafter it is diluted with 200 ml of water, and the pH of the aqueous phase is adjusted to 5 with 25% aqueous ammonia. The mixture is extracted then with 100, 80 and 60 ml of dichloromethane. The organic phases are combined, admixed with 100 ml of water, and the pH of the aqueous phase is adjusted to 10 with 25% aqueous ammonia. The mixture is shaken, the dichloromethane phase is separated, washed thrice with 100 ml of water, each, dried over anhydrous solid magnesium sulfate, filtered, and the filtrate is evaporated to dryness in vacuo. The 1.5 g of dry residue obtained are subjected to preparative thin layer chromatography. Kieselgel PF$_{254+366}$ grade silica gel plates, 20×20 cm in area and 1.5 mm in thickness, are applied as adsorbent, and a 10:3 mixture of benzene and acetonitrile is applied as solvent. The eluted substances are crystallized from methanol.

0.2134 g (13.2%) of ($\pm$)-9-bromo-14-oxo-15-hydroxy-E-homoeburnane-(3α,17α) are isolated from the upper spot. This substance (the product with the higher R$_f$ value) is identical with the compound of the highest R$_f$ value prepared as described in point (a).

0.6684 g (41.4%) of ($\pm$)-11-bromo-14-oxo-15-hydroxy-E-homoeburnane-(3α,17α), a product with lower R$_f$ value, are isolated from the middle spot. This substance is identical with the compound of the medium R$_f$ value prepared as described in point (a).

9-Bromo-14,15-dioxo-E-homoeburnane-(3α,17α) and 11-bromo-14,15-dioxo-E-homoeburnane-(3α,17α) are also formed in the reaction in an amount of about 5%. These compounds were identified by thin layer chromatography.

EXAMPLE 2

(+)-3(S),17(S)-9-Bromo-14-oxo-15-hydroxy-E-homoeburnane and (+)-3(S),17(S)-11-bromo-14-oxo-15-hydroxy-E-homoeburnane 1.10 g of ferric chloride hexahydrate are added to a solution of 1.45 g (4.02 mmoles) of (+)-3(S),17(S)-14-oxo-15-hydroxy-E-homoeburnane hydrochloride (m.p.: 240°-242° C.; [α]$_D^{20}$= +37.8°, c=1%, in pyridine) in 15 ml of glacial acetic acid, and 5 ml of a 1 molar bromine solution in glacial acetic acid are added slowly, at a rate of 0.5 ml/min., to the solution at room temperature under constant stirring. When the addition is complete the mixture is stirred for additional 9 hours at room temperature. When the reaction terminates the mixture is diluted with 200 ml of water, and the pH of the mixture is adjusted to 5 with 25% aqueous ammonia. The resulting solution is extracted with 100, 80 and 60 ml of dichloromethane. The organic phases are combined, admixed with 100 ml of water, and the pH of the aqueous phase is adjusted to 10 with 25% aqueous ammonia. The mixture is shaken, the dichloromethane phase is separated, washed thrice with 100 ml of water, each, dried over solid anhydrous magnesium sulfate, fitered, and the filtrate is evaporated in vacuo.

The 1.4 g of dry residue obtained are subjected to preparative thin layer chromatography. Kieselgel PF$_{254+366}$ grade silica gel plates, 20×20 cm in area and 1.5 mm in thickness, are applied as adsorbent, and a 10:3 mixture of benzene and acetonitrile is applied as solvent. The eluted substances are crystallized from methanol.

The substance with the higher R$_f$ value is (+)-3(S),17(S)-9-bromo-14-oxo-15-hydroxy-E-homo-eburnane. This compound is obtained with a yield of 0.2 g (12.3%) and melts at 104°–105° C. The empirical formula of the substance is C$_{20}$H$_{23}$BrN$_2$O$_2$ (mol.wt.: 403.33).

IR spectrum (KBr): $\nu_{max.}$ 3380 cm$^{-1}$ (—OH), 1690 cm$^{-1}$ (—CO).

$[\alpha]_D^{20}= +43.7°$ (c=1%, in chloroform).

The substance with the lower R$_f$ value is (+)-3(S),17(S)-11-bromo-14-oxo-15-hydroxy-E-homo-eburnane. This compound is obtained with a yield of 0.8 g (49.4%) and melts at 117°–119° C. The empirical formula of the substance is C$_{20}$H$_{23}$BrN$_2$O$_2$ (mol.wt.: 403.33).

IR spectrum (KBr): $\nu_{max.}$3350 cm$^{-1}$ (—OH), 1680 cm$^{-1}$ (—CO).

$[\alpha]_D^{20}= +18.3°$ (c=1%, in chloroform).

The 9- or 1+-Halogen-14-oxo-15-hydroxy-E-Homo-eburnane is treated with a halogenating agent /in the way disclosed in copending application No. R1-719/, preferably with phosphorus oxychloriddxx oxycloride, and the thus-obtained 9- or 11-halogen-14-oxo-15-halogen-E-homoeburnane is reacted with an alkali metal nitrite, e.g. sodium nitrite. The resulting 9- or 11-halogen-14-oxo-15-hydroxyimmino-E homoeburnane is transformed in a known way, e.g. by the method biscoxx disclosed in Belgian Patent Specification No. 765,006, into the corresponding halovincaminic acid ester, e.g. into the 11-bromo-vincamine having cerebral vasodilating effect, disclosed in the German Patent Specification No. 2,458,164.

What we claim is:

1. A process for the preparation of a racemic or optically active compound of the formulae (Ia) or (Ib),

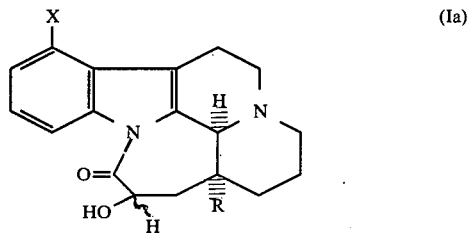
(Ia)

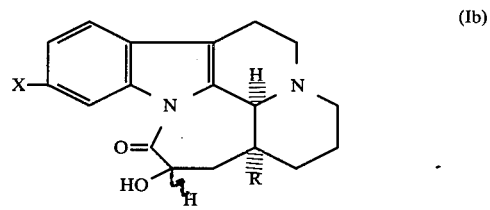
(Ib)

wherein R is C$_{1-6}$ alkyl and X is halogen, which comprises reacting a racemic or optically active 15-hydroxy-E-homoeburnane derivative of the formula (II),

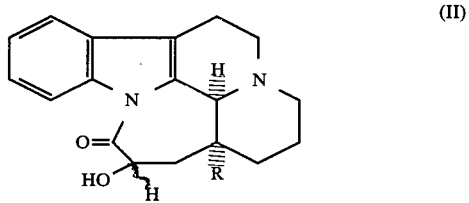
(II)

wherein R is as defined above; or an acid addition salt thereof, with a halogenating agent.

2. A process as claimed in claim 1 wherein elemental bromine is used as halogenating agent.

3. A process as claimed in claim 1 wherein halogenation is performed in the presence of a Lewis acid.

4. The process defined in claim 1 wherein the compounds of the formulae (Ia) and (Ib) formed in the reactio are separated from one another, and then either of the compounds is converted into an acid addition salt or is resolved.

* * * * *